US011613555B2

(12) United States Patent
Tilstam et al.

(10) Patent No.: US 11,613,555 B2
(45) Date of Patent: Mar. 28, 2023

(54) METHODS FOR ONAPRISTONE SYNTHESIS DEHYDRATION AND DEPROTECTION

(71) Applicant: Context Biopharma Inc., Philadelphia, PA (US)

(72) Inventors: Ulf Tilstam, Hoegaarden (BE); Stefan Proniuk, Austin, TX (US); Ferry Brands, Berghem (NL)

(73) Assignee: CONTEXT BIOPHARMA, INC., Philadelphia, PA (US)

( * ) Notice: Subject to any disclaimer, the term of this patent is extended or adjusted under 35 U.S.C. 154(b) by 0 days.

(21) Appl. No.: 17/034,598

(22) Filed: Sep. 28, 2020

(65) Prior Publication Data

US 2021/0221838 A1    Jul. 22, 2021

Related U.S. Application Data

(63) Continuation of application No. 15/825,697, filed on Nov. 29, 2017, now abandoned.

(60) Provisional application No. 62/428,401, filed on Nov. 30, 2016.

(51) Int. Cl.
*C07J 41/00* (2006.01)
*C07J 21/00* (2006.01)

(52) U.S. Cl.
CPC ......... *C07J 41/0083* (2013.01); *C07J 21/006* (2013.01)

(58) Field of Classification Search
CPC ........................... C07J 21/006; C07J 41/0083
See application file for complete search history.

(56) References Cited

U.S. PATENT DOCUMENTS

| | | | |
|---|---|---|---|
| 4,536,401 A * | 8/1985 | Neef | C07J 1/0081 514/173 |
| 4,742,000 A | 5/1988 | Greene | |
| 4,774,236 A | 9/1988 | Cook et al. | |
| 4,780,461 A | 10/1988 | Neef et al. | |
| 4,843,157 A | 6/1989 | Neef et al. | |
| 5,141,961 A | 8/1992 | Coapman | |
| 5,166,146 A | 11/1992 | Moguilewsky et al. | |
| 5,273,971 A | 12/1993 | Scholz et al. | |
| 5,283,190 A | 2/1994 | Traish et al. | |
| 5,446,036 A | 8/1995 | Scholz et al. | |
| 5,693,628 A | 12/1997 | Schubert et al. | |
| 6,093,707 A | 7/2000 | Cook et al. | |
| 6,143,754 A | 11/2000 | Chwalisz et al. | |
| 6,537,584 B1 | 3/2003 | Zentner et al. | |
| 6,750,015 B2 | 6/2004 | Horwitz et al. | |
| 6,900,193 B1 | 5/2005 | Kim et al. | |
| 7,678,781 B2 | 3/2010 | Fiordeliso et al. | |
| 8,121,365 B2 | 2/2012 | Pinard et al. | |
| 8,709,463 B2 | 4/2014 | Looney et al. | |
| 9,046,534 B2 | 6/2015 | Gilles | |
| 9,074,002 B2 | 7/2015 | Tonks et al. | |
| 9,193,757 B2 | 11/2015 | Proniuk | |
| 9,328,346 B2 | 5/2016 | Lee et al. | |
| 9,618,512 B2 | 4/2017 | Endou et al. | |
| 2003/0099641 A1 | 5/2003 | Smith et al. | |
| 2004/0072811 A1 | 4/2004 | Hoffmann et al. | |
| 2004/0121304 A1 | 6/2004 | Fuhrmann et al. | |
| 2004/0141980 A1 | 7/2004 | Ignjatovic et al. | |
| 2006/0063190 A1 | 3/2006 | Fischer et al. | |
| 2006/0111577 A1 | 5/2006 | Kim et al. | |
| 2007/0166372 A1 | 7/2007 | Huang et al. | |
| 2007/0166753 A1 | 7/2007 | Mass | |
| 2007/0167971 A1 | 7/2007 | Huey et al. | |
| 2008/0200440 A1 | 8/2008 | Fuhrmann et al. | |
| 2010/0150930 A1 | 6/2010 | Wilson et al. | |
| 2011/0003753 A1 | 1/2011 | Waxman et al. | |
| 2011/0053900 A1 | 3/2011 | Podolski et al. | |
| 2011/0293511 A1 | 12/2011 | Johns et al. | |
| 2012/0010790 A1 | 1/2012 | Kanayama et al. | |
| 2012/0140790 A1 | 6/2012 | Ali et al. | |
| 2012/0201865 A1 | 8/2012 | Dorairaju et al. | |
| 2012/0230983 A1 | 9/2012 | Muller et al. | |
| 2013/0018027 A1 | 1/2013 | Podolski et al. | |
| 2013/0029953 A1 | 1/2013 | Nickisch et al. | |
| 2013/0095170 A1 | 4/2013 | Gilles | |
| 2013/0316992 A1 | 11/2013 | Lange et al. | |
| 2013/0338016 A1 | 12/2013 | McDonough et al. | |
| 2014/0127219 A1 | 5/2014 | Sahin et al. | |
| 2014/0271819 A1 * | 9/2014 | Proniuk | A61K 45/06 424/450 |
| 2014/0363425 A1 | 12/2014 | Graham et al. | |
| 2015/0231155 A1 | 8/2015 | Proniuk | |
| 2015/0241432 A1 | 8/2015 | Berois et al. | |
| 2015/0241435 A1 | 8/2015 | Gilles | |
| 2015/0285803 A1 | 10/2015 | Gilles et al. | |
| 2016/0166583 A1 | 6/2016 | Zukiwski et al. | |

(Continued)

FOREIGN PATENT DOCUMENTS

| | | |
|---|---|---|
| CN | 1087090 A | 5/1994 |
| CN | 103483449 A | 1/2014 |

(Continued)

OTHER PUBLICATIONS

Ferland (Canadian Journal of Chemistry, Synthetic Cardenolides and Related Products. 111. Isocardenolides, 1974, 52, pp. 1652-1661. (Year: 1974).*
Neef et al (Steroids., New Steroids with Antiprogestational and Antiglucocorticoid Activities, 1984, 44(4), pp. 349-372).*
Kushner, P. et al., "Estrogen receptor pathways to AP-1" (2000) J Steroid Biochem Mol Biol 74: 311-317.
Lanari, C. et al., "Antiprogestins in breast cancer treatment: are we ready?", Endocrine-Related Cancer (2012) 19: R35-R50.
Lange, C. et al., "Progesterone Receptor Action: Translating Studies in Breast Cancer Models to Clinical Insights", Innov Endocrinol Cancer (2008) 7: 94-110.
Langmead, B. et al., "Ultrafast and memory-efficient alignment of short DNA sequences to the human genome." (2009) Genome Biol 10: R25.

(Continued)

*Primary Examiner* — Susanna Moore

(57) ABSTRACT

Methods and systems for making onapristone (ONA) using acidic hydrolysis and dehydration with sulfuric acid in an alcoholic solution are provided.

22 Claims, No Drawings

(56) References Cited

U.S. PATENT DOCUMENTS

| | | | |
|---|---|---|---|
| 2017/0088579 A1 | 3/2017 | Tilstam et al. | |
| 2017/0182065 A1 | 6/2017 | Brittain et al. | |
| 2017/0266204 A1 | 9/2017 | Proniuk et al. | |

FOREIGN PATENT DOCUMENTS

| | | | | |
|---|---|---|---|---|
| DE | 3321826 A1 | 12/1984 | | |
| EP | 0129499 A2 | 12/1984 | | |
| EP | 0277676 A1 | 8/1988 | | |
| EP | 0447014 A2 | 9/1991 | | |
| EP | 0803250 A1 | 10/1997 | | |
| EP | 2075246 A1 | 7/2009 | | |
| JP | H07509218 A | 10/1995 | | |
| JP | 2011511011 A | 4/2011 | | |
| JP | 2012533539 A | 12/2012 | | |
| WO | 1998031702 A1 | 7/1998 | | |
| WO | 2002072813 A1 | 9/2002 | | |
| WO | 2006010097 A2 | 1/2006 | | |
| WO | 2006111856 A1 | 10/2006 | | |
| WO | 2007078599 A2 | 7/2007 | | |
| WO | 2008128783 A2 | 10/2008 | | |
| WO | 2009025759 A1 | 2/2009 | | |
| WO | 2009134725 A2 | 11/2009 | | |
| WO | 2012083017 A2 | 6/2012 | | |
| WO | 2012087983 A1 | 6/2012 | | |
| WO | 2012122514 A1 | 9/2012 | | |
| WO | 2013016725 A1 | 1/2013 | | |
| WO | WO-2013016725 A1 * | 1/2013 | ............ | C07J 1/0088 |
| WO | 2013052652 A1 | 4/2013 | | |
| WO | 2013086379 A3 | 8/2013 | | |
| WO | 2014093918 A1 | 6/2014 | | |
| WO | 2014164861 A1 | 10/2014 | | |
| WO | 2014197653 A2 | 12/2014 | | |
| WO | 2016154203 A1 | 9/2016 | | |
| WO | 2017192567 A1 | 11/2017 | | |
| WO | 2018067198 A1 | 4/2018 | | |

OTHER PUBLICATIONS

Lasonos, A. et al., "Scientific Review of Phase I Protocols With Novel Dose-Escalation Designs: How Much Information Is Needed?", Journal of Clinical Oncology (2015) JCO. 2014.59.8466.
Lieberman, B. et al., "The constitution of a progesterone response element." (1993) Mol Endocrinol 7: 515-527.
Liu, Z. et al., "Sequential recruitment of steroid receptor coactivator-1 (SRC-1) 5 and p300 enhances progesterone receptor-dependent initiation and reinitiation of transcription from chromatin." (2001) Proc Natl Acad Sci U S A 98: 12426-12431.
Longacre, T. "A correlative morphologic study of human breast and endometrium in the menstrual cycle." (1986) Am J Surg Pathol 10: 382-393.
Lupien, M. et al., "FoxA 1 translates epigenetic signatures into enhancer-driven lineage-specific transcription." (2008) Cell 132: 958-970.
Macquarrie, K. et al., "Genome-wide transcription factor binding: beyond direct target regulation." (2011) Trends Genetics 27: 141-148.
McGowan et al., "Cytoskeletal Responsiveness to Progestins is Dependent on Progesterone Receptor A Levels," Journal of Molecular Endocrinology, 2003, 31, pp. 241-253.
McKenna, N. et al., "Combinatorial control of gene expression by nuclear receptors and coregulators." (2002) Cell 108: 465-474.
Metzger, E. et al., "LSD1 demethylates repressive histone marks to promote androgen-receptor-dependent transcription.", Nature (2005) 437:436-439.
Meuleman et al., "Morphological and Biochemical Characterization of a Human Liver in a uPA-SCID Mouse Chimera", Hepatology (2005) 41 (4); 847-856.
Mortazavi, A. et al., "Mapping and quantifying mammalian transcriptomes by RNA-Seq.", (2008) Nat Methods 5: 621-628.

Mortel, R. et. al., "Heterogeneity and Progesterone-Receptor Distribution in Endometrial Adenocarcinoma", Cancer (1984) 53:113-116.
Mote et al. "Detection of progesterone receptor forms A and B by immunohistochemical analysis", (2001) J. Clin. Pathol. 54: 624-630.
Mote, P. "Relative expression of progesterone receptors A and B in premalignant and invasive breast lesions", Breast Cancer Research (2000) 2 (Suppl 1) P2.01 doi:1 0.1186/bcrl 03.
Mote, P. et al., "Loss of co-ordinate expression of progesterone receptors A and B is an early event in breast carcinogenesis", Breast Cancer Res Treat (2002) 72(2): 163-72.
Mote, P. et al., "Progesterone receptor isoforms in normal and malignant breast", Ernst Schering Found Symp Proc. (2007) (1):77-107.
Mou et al., "Potent dried drug nanosuspensions for oral bioavailability enhancement of poorly soluble drugs with pH-dependent solubility", (2011) International Journal of Pharmaceutics 413, pp. 237-244.
Murtagh, J. et al., "The Nuclear Factor I (NFI) gene family in mammary gland development and function.", (2003) J Mammary Gland Biol Neoplasia 8: 241-254.
Nadji, M. "Immunohistochemistry of Estrogen and Progesterone Receptors Reconsidered: Experience With 5,993 Breast Cancers", Anatomic Pathol. (2005) 123:21-27.
Neef et al., "New Steroids by Simmons-Smith Methyenation and Subsequent Rearrangement", J_ Org_ Chem., (1987) vol. 52, No. 18 pp. 4143-4146.
Neef, G. et al., "New steroids with antiprogestational and antiglucocorticoid activities", (1984) 44, 349-372.
Nelson, C. et al., "Determinants of DNA sequence specificity of the androgen, progesterone, and glucocorticoid receptors: evidence for differential steroid receptor response elements." (1999) Mol Endocrinol 13: 2090-2107.
Non-Final Office Action issued in U.S. Appl. No. 14/942,809, dated Jan. 6, 2017.
Non-Final Office Action dated Apr. 8, 2021 U.S. Appl. No. 16/720,425.
Non-Final Office Action dated Feb. 19, 2019 in U.S. Appl. No. 15/464,085.
Non-Final Office Action dated Feb. 8, 2019 in U.S. Appl. No. 15/378,004.
Non-Final Office Action dated Jan. 23, 2019 in U.S. Appl. No. 14/681,032.
Non-Final Office Action dated Mar. 6, 2015 in U.S. Appl. No. 14/205,694.
Non-Final Office Action dated May 13, 2019 in U.S. Appl. No. 14/698,100.
Non-Final Office Action dated May 15, 2019 in U.S. Appl. No. 14/942,809.
Non-Final Office Action dated Nov. 27, 2018 in U.S. Appl. No. 15/825,697.
Non-Final Office Action, dated Aug. 5, 2021, issued in U.S. Appl. No. 17/034,598.
Non-Final Office Action, dated Jan. 17, 2018, issued in U.S. Appl. No. 15/825,697.
Non-Final Office Action, dated Oct. 7, 2021, issued in U.S. Appl. No. 16/720,425.
Non-Final Office Action, dated Sep. 1, 2021, in U.S. Appl. No. 17/035,544.
Notice of Allowance received in U.S. Appl. No. 14/942,809 dated May 27, 2020.
Notice of Allowance received in U.S. Appl. No. 15/274,555 dated Jan. 15, 2019.
Notice of Allowance received in U.S. Appl. No. 15/378,004 dated Sep. 25, 2019.
Notice of Allowance received in U.S. Appl. No. 15/825,697 dated Aug. 9, 2018.
Onate, S. et al., "Sequence and characterization of a coactivator for the steroid hormone receptor superfamily." (1995) Science 270: 1354-1357.
Pearson, P. Wienkers, editors. Handbook of drug metabolism:, New York: Informa Healthcare; 2009. pp. 445-464.

(56) References Cited

OTHER PUBLICATIONS

Pierrou, S. et al., "Cloning and characterization of seven human forkhead proteins: binding site specificity and DNA bending." (1994) EMBO J 13: 5002-5012.
Press, M. et al. "Comparison of different antibodies for detection of progesterone receptor in breast cancer", Steroids (2002) 67:799-813.
Puma, et al., Dimensionless analysis of slurry photocatalytic reactors using two-flux and six-flux radiation absorptionscattering models, Catalysis Today, 2007, 122, pp. 78-90.
Puma, G. L., "Photocatalytic oxidation of multicomponent systems of herbicides: scale-up of laboratory kinetics rate data to plant scale" Catal. Today 2007, 124-132.
Rayasam, G. et al., "Ligand-specific dynamics of the progesterone receptor in living cells and during chromatin remodeling in vitro.", Mol Cell (2005) Biol 25: 2406-2418.
Final Office Action dated Feb. 20, 2020 U.S. Appl. No. 14/942,809.
Final Office Action dated May 11, 2018 in U.S. Appl. No. 15/378,004.
Final Office Action dated Oct. 24, 2019 U.S. Appl. No. 15/464,085.
Friedman, J. et al., "The Foxa family of transcription factors in development and metabolism." (2006) Cell Mol Life Sci 63: 2317-2328.
Garcia-Bassets, I. et al., "Histone methylation-dpendent mechanisms impose ligand dependency for gene activation by nuclear receptors." (2007) Cell 128: 505-518.
Goyeneche, A. et al., "Antiprogestins in gynecological diseases" Reproduction (2015) 149: RI5-R33.
Graham, D. et al., "Determination of the activated form of the progesterone receptor (PR) in endometrial cancer (EC)", J. Clin. Oncol. (2013); 3J (suppl; abstr 5602).
Graham, J. "Progesterone receptors—animal models and cell signaling in breast cancer Expression and transcriptonal activity of progesterone receptor A and progestereone receptor B in mamalian cells", Breast Cancer Res (2002) 4: 187-190.
Graham, J. et al., "Altered progesterone receptor isoform expression remodels progestin responsiveness of breast cancer cells." (2005) Mol Endocrinol 19: 2713-2735.
Graham, J. et al., "Characterization of progesterone receptor A and B expression in human breast cancer." (1995) Cancer Res 55: 5063-5068.
Graham, J. et al., "DNA replication licensing and progenitor numbers are increased by progesterone in normal human breast." (2009) Endocrinology 150: 3318-3326.
Graham, J. et al., "Expression and transcriptional activity of progesterone receptor A and progesterone receptor B in mammalian cells ", Breast Cancer Research (2002) 4(5):187-190.
Graham, J. et al., "Physiological action of progesterone in target tissues." Endocr Rev (1997) 18: 502-519.
Grunberg et al., "Long-Term Administration of Mifepristone (RU486): Clinical Tolerance During Extended Treatment of Meningioma", Cancer Investigation, Jun. 11, 2009, 24:8, pp. 727-733.
Guohua et al., "Synthesis of Progesterone Receptor Antagonist ZK98299," Zhongguo Yaoke Daxue Xuebao (1992), 23 (4), 209-12.
Gwin K., et al., "Breast carcinoma with chondroid differentiations clinicopathologic study of 21 triple negative (ER-, PR-,Her2/neu-)cases." Int J Surg Pathol. (2010) 8 (1):27-35.
Hancock, B. et al., "Characteristics and Significance of the Amorphous State in Pharmaceutical Systems" Journal of Pharmaceutical Sciences (1997) vol. 88, No. I, pp. 1-12.
Heinz, S. et al., "Simple combinations of lineage-determining transcription factors prime cis-regulatory elements required for macrophage and B cell identities ", (2010) Mol Cell 38: 576-589.
Heydarzadeh et al., "Catalyst-free conversion of alkali cellulose to fine carboxymethyl cellulose at mild conditions", (2009) World Appl. Sci. J. 6 (4) 564-569.
Hopp, T. et al., "Breast Cancer Patients with Progesterone Receptor PR-A-Rich Tumors Have Poorer Disease-Free Survival Rates", Clin Cancer Res. (2004) 10; 2751.
Hubler, T. et al., "Intronic hormone response elements mediate regulation of FKBP5 by progestins and glucocorticoids." (2004) Cell Stress Chaperones 9: 243-252.
Hurtado, A. et al., "FOXA 1 is a key determinant of estrogen receptor function and endocrine response." (2011) Nat Genet 43: 27-33.
Hutt, E. et al., "Clinical and pathological correlation of the activated form of the progesterone receptor (APR) in Endometrial Cancer (EC)", ECC 2013, 1.002.
International Search Report and Written Opinion dated Feb. 27, 2017 for International Patent Application No. PCT, US2016/066420.
International Search Report of International Patent Application No. PCT/US2012058732 dated Dec. 11, 2012.
International Application No. PCT/US2014/023651, Written Opinion dated Jul. 28, 2014, 11 pgs.
International Preliminary Report on Patentability issued in Internaional Patent Application No. PCT/IB2015/058369 dated May 2, 2017.
International Search Report and Written Opinion for International Patent Application No. PCT/US2017/023256 dated Jun. 16, 2017.
International Search Report and Written Opinion of PCT Application No. PCT/US2016/053435 dated Dec. 15, 2016.
International Search Report issued in International Patent Application No. PCT/IB2015/058369 dated Jan. 25, 2016.
International Search Report of corresponding PCT Application No. PCT/IB 2015/000312 dated Jul. 22, 2015.
International Search Report of PCT Application No. PCT/US2015/060940 dated Jan. 28, 2016.
Ishibashi, H. et al., "Progesterone receptor in non-small cell lung cancer—a potent prognostic factor and possible target for endocrine therapy", Cancer Res. (2005) 65 (14) 6450-8.
Jang et al, "Cytochrome P4503A4-Mediated N-Demethylation of the Antiprogestins Lilopristone and Onapristone", The American Society for Pharmacology and Experimental Therapeutics (1997) vol. 25, No. 10, 1119-1122.
Ji, H. et al., "An integrated software system for analyzing Ch IP-chip and ChIP-seq data." (2008) Nat Biotechnol 26: 1293-1300.
John, S. et al. "Chromatin accessibility pre-determines glucocorticoid receptor binding patterns.", (2011) Nat Genet 43: 264-268.
Jonat et al., "The clinical efficacy of progesterone antagonists in breast cancer", Endocrine Therapy of Breast Cancer, (2002) pp. 117-124.
Jonat, W. et al., "Randomized phase 2 study of lonaprisan as second line therapy for progesterone receptor positive breast cancer", Ann Oncol (2013) 24: 2543-2548.
Joseph, R. et al. "Integrative model of genomic factors for determining binding site selection by estrogen receptor-alpha." (2010) Mol Sys! Biol 6: 456.
Kabasakalian, Peter et al., "Solubility or Some Steroids in Water", Journal of Pharmaceutical Sciences, 55(6): 642 (2006).
Kamimura, H. et al., "Assessment of chimeric mice with humanized liver as a tool for predicting circulating human metabolites drug metab pharmacokinet", (2010) 25(3): 223-235.
Kao, L. et al., "Global gene profiling in human endometrium during the window of implantation." (2002) Endocrinology 143: 2119-2138.
Kawaguchi, Y. et al, "Drug and crystal polymorphism", Journal of Human Environmental Engineering, 2002, vol. 4, No. 2, p. 310-317.
Kim, J. et al., "Progesterone Action in Endometrial Cancer, Endometriosis, Uterine Fibroids, and Breast Cancer", Endocrine Rev. (2013) 34: 130-162.
Klijn et al., Progesterone antagonists and progesterone antagonist and progesterone receptor modulation in the treatment of beast cancer, (2000) Steroids, v. 65 pp. 825-830.
Knutson, et al., "Phosphorylated and sumoylation-deficient progesterone receptors drive proliferative gene signatures during breast cancer progession", Breast Cancer Research, 2012, vol. 14: R95.
Kocienski, Carbonyl Protecting Groups, 3rd Edition, Thieme (2005), pp. 58-59.
Koivisto-Korander, R. "Mifepristone as treatment of recurrent progesterone receptor-positive uterine leiomyosarcoma", Obstetrics and Gynecology (2007) 109: 512-514.

(56) References Cited

OTHER PUBLICATIONS

Kojima, T., "To improve efficiency of selecting crystal shape with drug development", Journal of Pharmaceutical Science and Technology, (2008) vol. 68, No. 5, p. 344-349.
Krum, S. et al., "Unique ERalpha cistromes control cell type-specific gene regulation." (2008) Molecular Endocrinology 22: 2393-2406.
Reddy, T. et al. "Genomic determination of the glucocorticoid response reveals unexpected mechanisms of gene regulation." (2009) Genome Res 19: 2163-2171.
Reich, M. et al. (2006) GenePattern 2.0. Nat Genet 38: 500-501.
Rezai et al., "A single-dose PK study of onapristone including the effect of food on absorption", Cancer Chemother. Pharmacol. (2015) 76: 171-177.
Rezai, K. et al., "Population pharmacokinetic (PPK) modeling of onapristone in patients (pts) with progesterone receptor (PR)-expressing cancers", AACR Annual Meeting (2015) Abstract 4523.
Richer, J. et al., "Differential gene regulation by the two progesterone receptor isoforms in human breast cancer cells." (2002) J Biol Chem 277: 5209-5218.
Robertson et al. "Onapristone, a progesterone receptor antagonist, as first-line therapy in primary breast cancer", (1999) vol. 35, Issue 2, pp. 214-218.
Roschke, A. et al., "Karyotypic complexity of the NCI-60 drug-screening panel." (2003) Cancer Res 63: 8634-8647.
Rossouw, J. et al., Risks and benefits of estrogen plus progestin in healthy postmenopausal women: principal results from the Women's Health Initiative randomized controlled trial. (2002) JAMA 288: 321-333.
Scarpin, K. et al., "Progesterone action in human tissues: regulation by progesterone receptor (PR) isoform expression, nuclear positioning and coregulator expression." (2009) Nucl Recept Signal 7: e009.
Schlogl S. et al., "Characteristics of the photochemical prevulcanization in a falling film photoreactor" J. App. Polymer Science, 2012, 124, 3478-3486.
Search Report of International Patent Application No. PCT/US2012/058732 dated Dec. 11, 2012.
Search Report of International Patent Application No. PCT/US2015/024792, dated Aug. 7, 2015.
Shi, et al., "Antigen retrieval immunohistochemistry under the influence of pH using monoclonal antibodies", Journal of Histochemistry & Cytochemistry (1995) vol. 43{2}, pp. 193-201.
So, A. et al., "Determinants of cell- and gene-specific transcriptional regulation by the glucocorticoid receptor." PLoS Genetics (2007) vol. 3, Issue 6; 0927-0938.
Streuli, C. et al., "Stat5 as a target for regulation by extracellular matrix.", (1995) J Biol Chem 270: 21639-21644.
Tang, Q. et al., "A comprehensive view of nuclear receptor cancer cistromes." (2011) Cancer Res 71: 6940-6947.
Telleria et al., "Antiprogestins in Ovarian Cancer. Ovarian Cancer—Clinical and Therapeutic Perspectives, DOI: 10.5772/25269", (2012) 207-230.
Thike et al., "Triple-negative breast cancer; clnicopathological characteristics and relationship with basal-like breast cancer," Modem Pathology, 2010; 23; pp. 123-133.
Tseng, L. et al., "Progesterone receptor (hPR) upregulates the fibronectin promoter activity in human decidual fibroblasts." (2003) DNA Cell Biol 22: 633-640.
Vicent, G. et al., "Chromatin remodeling and control of cell proliferation by progestins via cross talk of progesterone receptor with the estrogen receptors and kinase signaling pathways." (2006) Ann N Y Acad Sci 1089: 59-72.
Vicent, G. et al., "Minireview: role of kinases and chromatin remodeling in progesterone signaling to chromatin." Mol Endocrinol (2010) 1-11.
Vicent, G. et al., "Two chromatin remodeling activities cooperate during activation of hormone responsive promoters." PLoS Genet (2009) vol. 5, Issue 7: 1-13.
Vicent, G. et al., Nuclear factor 1 synergizes with progesterone receptor on the mouse mammary tumor virus promoter wrapped around a histone H3/H4 tetramer by facilitating access to the central hormone-responsive elements. (2010) J Biol Chem 285: 2622-2631.
Wang, D. et al. "Reprogramming transcription by distinct classes of enhancers functionally defined by eRNA." Nature (2011) 1-25.
Wang, Q. et al., A hierarchical network of transcription factors governs androgen receptor-dependent prostate cancer grow1h. (2007) Mol Cell 27: 380-392.
Welboren, W. et al., "ChIP-Seq of ERalpha and RNA polymerase II defines genes differentially responding to ligands." (2009) EMBO J 28: 1418-1428.
Wizinger et al., Triphenymethanfarbstoffe aus Thiodiphenylamin undPhenoxazin, Helvetica Chimica Acta, (1952) vol. 35, pp. 316-329.
Written Opinion for PCT/US2017/023256, dated Jun. 16, 2017.
Written Opinion issued in International Patent Application No. PCT/IB2015/058369 dated Jan. 25, 2016.
Written Opinion of International Patent Application No. PCT/US2012/058732, dated Dec. 11, 2012.
Yamano, M., "Approach to Crystal Polymorph in Process Research of New Drug", Journal of Synthetic Organic Chemistry, (2007) vol. 65, No. 9, p. 907(69)-913(75).
Yin, P. et al. "Genome-wide progesterone receptor binding: cell type-specific and shared mechanisms in T47D breast cancer cells and primary leiomyoma cells." (2012) PLoS One 7: e29021.
Yin, P. et al., "Transcription Factor KLFI 1 Integrates Progesterone Receptor Signaling and Proliferation in Uterine Leiomyoma Cells", Cancer Res. (2010) 70(4); 1722-30.
Zala et al., "Laboratory Techniques of purification and isolation", Int. J. Drug Dev. & Res., (2012) vol. 4, No. 2, pp. 41-455.
Zukiwski et al., "Independent characterization by duel staining of progesterone receptor (PR) and estrogen receptor (ER) in breast cancer (BC)", Proc ASCO, abstract No. 118076 (2003).
A0A2V9M896_9BACT, UniProtKB Accession No. A0A2V9M896_9BACT, Siaidase domain-containing protein, Sep. 12, 2018 [Online]. Retrieved on May 22, 2020. Retrieved from the Internet: < URL: https://www.uniprot.org/Uniprot/A0a2v9m896 > Entire document.
Ace, C. et al., "Microarray profiling of progesterone-regulated endometrial genes during the rhesus monkey secretory phase." (2004) Reprod Biol Endocrinol 2: 54.
Ariga, N. et al: "Progesterone receptor A and B isoforms in the human breast and its disorders", (2001) Jpn J. Cancer Res. vol. 92, No. 3, 302-308.
Arnett-Mansfield, et al., "Focal Subnuclear Distribution of Progesterone Receptor is Ligand Dependent and Associated with Transcriptional Activity," Mol Endocrinol, Jan. 2007, vol. 2, No. 1, pp. 14-29.
Arnett-Mansfield, et al., "Subnuclear Distribution of Progesterone Receptors A and B in Normal and Malignant Endometrium", J Clin Endocrinol Metab, (2004) vol. 89, No. 3, pp. 1429-1442.
Bailey, T. et al., "MEME: discovering and analyzing DNA and protein sequence motifs." (2006) Nucleic Acids Res 34: W369-373.
Bailey, T., et al., "The value of position-specific priors in motif discovery using MEME." (2010) BMC Bioinformatics 11: 179.
Baillie et al., "Role of Biotransformation in Drug-Induced Toxicity: Influence of Intra- and Inter-Species Differences in Drug Metabolism", (2011) 26(1): 15-29.
Ballare, C. et al., "Nucleosome-Driven Transcription Factor Binding and Gene Regulation." (2013) Molecular Cell 49, 1-13.
Bamberger et al. "Progesterone receptor isoforms, PR-Band PR-A, in breast cancer: Correlations with clinicopathologic tumor parameters and expression of AP-1 factors", Horm Res (2000) CH. vol 54: 32-37.
Beck, C. A. et al., "Two Types of Anti-progestins Have Distinct Effects on Site-specific Phosphorylation of Human Progesterone Receptor", The Journal of Biological Chemistry (1996) 271: 1209-1217.
Beguelin, W. et al., "Progesterone receptor induces ErbB-2 nuclear translocation to promote breast cancer grow1h via a novel transcriptional effect: ErbB-2 function as a coactivator of Stat3." (2010) Mol Cell Biol 30: 5456-5472.

(56) References Cited

OTHER PUBLICATIONS

Belikov, S. et al., "FoxA 1 binding directs chromatin structure and the functional response of a glucocorticoid receptor-regulated promoter." (2009) Mol Cell Biol 29: 5413-5425.
Benagiano, G. et al., "Selective progesterone receptor modulators 3: use in oncology, endocrinology and psychiatry", Expert Opin. Pharmacother (2008) 9:2487-2496.
Beral, V. et al., "Breast cancer and hormone-replacement therapy in the Million Women Study." (2003) Lancet 362: 419-427.
Beral, V. et al., "Breast Cancer Risk in Relation to the Interval Between Menopause and Starting Hormone Therapy." (2011) J Natl Cancer Inst 103: 296-305.
Bergström et al. "Accuracy of calculated pH-dependent aqueous drug solubility", European J. Pharmaceutical Sciences, (2004) vol. 22, pp. 387-398.
Bernardo, G. et al., FOXA1 is an essential determinant of ERalpha expression and mammary ductal morphogenesis. (2010) Development 137: 2045-2054.
Blankenstein, M. et al., "Occurrence, regulation, and significance of progesterone receptors in human meningiome", Steroids (2000) 65: 795-800.
Bolton, C. et al. "Cell- and gene-specific regulation of primary target genes by the androgen receptor.", (2007) Genes Dev 21: 2005-2017.
Bonkhoff, H. et al., "Progesterone Receptor Expression in Human Prostate Cancer: Correlation With Tumor Progression. Prostate" (2001) 48: 285-291.
Bonneterre et al., "Abstract P5-02-13: Triple negative breast cancer the impact of isotype-specific progesterone receptor antibodies on the diagnosis results Cancer Researeh", (2015) vol. 75; 9, pp. P5-02-13, 1538-7445.
Bonneterre, J. et al., "Development of a technique to detect the activated form of the progesterone receptor and correlation with clinical and histopathological characteristics of endometrioid adenocarcinoma of the uterine corpus", Gynecologic Oncology (2015) doi: 10.1016/j.ygyno.2015.06.037.
Boonkasemsanti et al. "Arzneimittel-Forschung", Arzneim.-Forsch. (1989) vol. 39, No. 2, pp. 195-199.
Borthwick, J. et al., "Determination of the transcript profile of human endometrium.", (2003) Mol Hum Reprod 9: 19-33.
Bravieri, R. et al., "Different DNA contact schemes are used by two winged helix proteins to recognize a DNA binding sequence." (1997) Nucleic Acids Res 25: 2888-2896.
Cameron, S. et al, "Critchley HOD, Buckley CH et al. The effects of post-ovulatory administration of onapristone on the development of a secretory endometrium", Human Reproduction (1996) 11 (1):40-49.
Cameron, S. et al., "Effects of onapristone on postmenopausal endometrium. Steroids", (2003) 68: 1053-1059.
Cantillo (Kappe) et al. "A Continuous-Flow Protocol for Light-Induced Benzylic Fluorinations" J. Org. Chem., 2014, 79 (17), pp. 8486-8490.
Carroll, J. et al., "Genome-wide analysis of estrogen receptor binding sites." (2006) Nat Genet 38: 1289-1297.
Chan, S. Y., "The development of PVP-based solid dispersions using hot melt extrusion for the prepaation of immediate release formulations," Thesis for PhD, (2013) School of Pharmacy University of East Anglia.
Chapman et al., "GenePattern 2.0; Nature Genetics" Nature Publishing Group (2006); vol. 38, No. 5.
Chen et al., "A facile nanoaggregation strategy for oral delivery of hydrophobic drugs by utilizing acid-base neutralization reactions", (2008) Nanotechnology 19: 375104, pp. 1-7.
Chlebowski, R. et al., "Estrogen plus progestin and breast cancer incidence and mortality in postmenopausal women." (2010) JAMA 304: 1684-1692.
Cicatiello, L. et al., "Estrogens and progesterone promote persistent CCND1 gene activation during G1 by inducing transcriptional derepression via c-Jun/c-Fos/estrogen receptor (progesterone receptor) complex assembly to a distal regulatory element and recruitment of cyclin D1 to its own gene promoter." (2004) Mol Cell Biol 24: 7260-7274.
Cirillo LA, Zaret KS (2007) Specific interactions of the wing domains of FOXA 1 transcription factor with DNA. J Mol Biol 366: 720-724.
Clarke, C. et al., "Monoclonal antibodies to human progesterone receptor: characterization by biochemical and immunohistochemical techniques." (1987) Endocrinology 121: 1123-1132.
Clarke, C. et al., "Non-Overiapping Progesterone Receptor Cistromes Contribute to Cell-Specific Transcriptional Outcomes." (2012) PLoS ONE 7(4): e35859. doi:10.1371/journal.pone.0035859.
Clarke, C. et al., "Progestin regulation of cellular proliferation." (1990) Endocr Rev 11: 266-301.
Cottu, P. et al., "Onapristone (ONA) in progesterone receptor (PR)-expressing tumors: Efficacy and biomarker results of a dose-escalation phase 1 study", J. Clin. Oncol. (2015) 33 (suppl; abstr 5593).
Croxatto, H. et al., "Effect of the antiprogestin onapristone on follicular growth in women", Human Reproduction (1994) 9: 1442-1447.
Dorwald, Zaragoza et al., "Side Reactions in Organic Synthesis", Wiley-VCH Verlang GmbH & Co. KGaA, Weinheim, Preface, p. IX (2005).
EP15776251.9 partial supplementary European search report (R 164 EPC) dated Nov. 7, 2017.
Etreby, et al., "Antitumor Activity of Mifepristone in the Human LNCaP, LNCaP-C4, and LNCaP-C4-2 Prostate Cancer Models in Nude Mice", The Prostate, 2000, vol. 42, No. 2, pp. 99-106.
Examination Report of Australian Patent Application 2012318618, dated Aug. 9, 2016.
Examination Report of New Zealand Patent Application No. 623140 dated Dec. 8, 2014.
Extended European Search Report of European Patent Application No. 12837954.2 dated Apr. 17, 2015.
Faivre, E. et al., "Progesterone receptor rapid signaling mediates serine 345 phosphorylation and tethering to specificity protein 1 transcription factors." (2008) Mol Endocrinol 22: 823-837.
Ferland "Synthetic Cardenolides and Related Products. III. Isocardenolides," Canadian Journal of Chemistry (1974) 52,, pp. 1642-1661.
Final Office Action dated Aug. 27, 2019 U.S. Appl. No. 15/825,697.
Dong, "Evaluation of solid state properties of solid dispersions prepared by hot-melt extrusion and solvent co-precipitation", International Journal of Pharmaceutics (2008) 355, pp. 141-149.
Stitt, et al., "Scale-up of Chemical Reactions", Process Understanding (2011) pp. 155-198.
Paul, "Design of Reaction Systems for Specialty Organic Chemicals", Chemical Engineering Science, (1988) vol. 43, No. 8, pp. 1773-1782.
Tanaka, et al., "Large-scale synthesis of immunoactivating natural product, pristane, by continuous microfluidic dehydration as the key step". Org Lett. (2007) vol. 9, No. 2, pp. 299-302.

* cited by examiner

METHODS FOR ONAPRISTONE SYNTHESIS DEHYDRATION AND DEPROTECTION

This application is a continuation of U.S. patent application Ser. No. 15/825,679, filed on Nov. 29, 2017, which claims priority to U.S. Provisional application No. 62/428,401, filed on Nov. 30, 2016, each of which is hereby incorporated by reference in its entirety.

All references cited herein, including but not limited to patents and patent applications, are incorporated by reference in their entirety.

BACKGROUND

Onapristone (ONA) is an anti-progestin drug and progesterone receptor antagonist which was originally developed for contraceptive use. However, it has demonstrated substantial activity in advanced breast cancer. It is thought that ONA binds to the progesterone receptor (PR), preventing the PR from binding to DNA, thereby inhibiting or eliminating PR-induced transcription. See, e.g., Klijn et al., Progesterone antagonists and progesterone receptor modulation in the treatment of breast cancer, Steroids, v. 65, pp. 825-830 (2000); Jonat et al., The clinical efficacy of progesterone antagonists in breast cancer, Endocrine Therapy of Breast Cancer, pp. 117-124.

European Patent Number 0129499 (499 Patent) refers to a process for the deprotection and dehydration of the final intermediate to obtain ONA as a crude mixture. According to the '499 Patent, any mineral or organic acid can be used for the removal of the ketal in the 3-position, the dehydration of the 5-hydroxy group, and the removal of the protecting group on the primary hydroxyl group at C23. Solvents for the process should be aqueous methanol, ethanol, or acetone, and the mineral acids should be used in catalytic amounts, according to the '499 Patent.

The '499 Patent discloses that heating the precursor to ONA in 70% acetic acid at 50° C. for 3 hours is the best process for the removal of the protecting groups and the dehydration of the 5-OH group. The '499 patent further teaches that (1) the reaction mixture is diluted with water, (2) neutralized with aqueous ammonia to pH 10.2, (3) extracted with ethyl acetate, and (4) after removal of the solvent, the reaction mixture is chromatographically purified to crystallize the ONA with a 70% yield of 70%.

The same method was disclosed in Neef, G., *Steroids*, 1984, 44, 349. The authors reported no yield from the reaction. Chen, G. et al. *Zhogguo Yaoke Daxue Xuebao*, 1992, 23, 209 described the use of the same method at 50° C., but shortened the reaction time to 1 hour. After workup and chromatographic purification, the authors isolated ONA with a yield of 56% through crystallization. The THP protected 17ß-OH intermediate was isolated from the reaction mixture. This intermediate is formed during the reaction due to a rearrangement of the THP protecting group from the primary alcohol to the tertiary alcohol in the 17 position. THP protected 17ß-OH has been found to be the most stable with respect to hydrolytic conditions.

Other reaction methods include the use of P-Toluenesulfonic acid for hydrolysis of the ketal in C3, and dehydration of C5-OH (U.S. Pat. No. 5,693,628); sulfuric acid in methanol for the hydrolysis of ketals and dehydration of C5-OH (WO 2013016725); sulfuric acid in acetone (WO 1998031702); sulfuric acid in ethanol for the hydrolysis ketals and for the dehydration of C5-OH (U.S. Pat. No. 6,900,193) and HCl in methanol for the hydrolysis of the ketal and dehydration of the C5-OH (Gao, G. et al, Faming Zhuanti Shenqing Gonkai CN1087090). In each of the above cases, chromatographic purification prior to crystallization was necessary, and the structures of the starting material contained the C13 ß methyl group.

SUMMARY

In one aspect, methods are described herein for the deprotection and dehydration of the compound of Formula I:

Formula I to the compound of Formula II:

Formula II

In one aspect, the compound of Formula I is the precursor of Formula II onapristone (ONA). The compound of Formula I is also referred to herein as Steroid 1.

In another aspect, the compound of Formula II is the final product, onapristone (ONA).

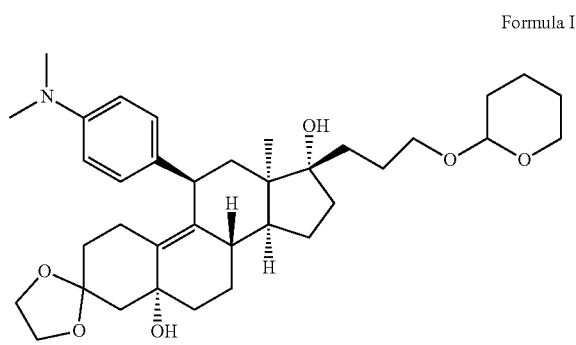

Steroid 1

-continued

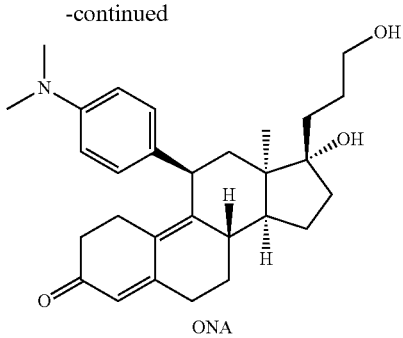

ONA

DETAILED DESCRIPTION

Before describing an exemplary aspect described herein, it is to be understood that the invention is not limited to the details of construction or process steps set forth in the following description. The aspect described herein is capable of being practiced or being carried out in various ways.

Aspects described herein provide methods of making onapristone by reacting the compound of Formula I:

Formula I

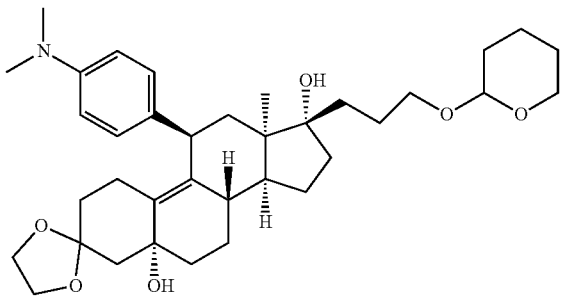

with sulfuric acid in a solvent to deprotect the compound of Formula I. In this aspect, the reaction temperature is maintained below about 60° C.; the reaction is neutralized with an inorganic base to form a solution; and the compound of Formula II (onapristone) is extracted from the solution.

Formula II

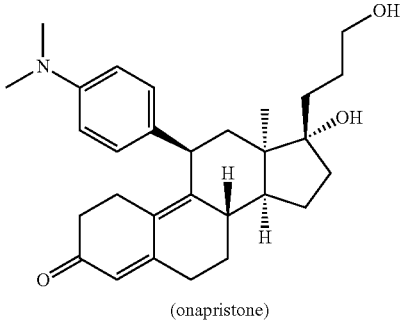

(onapristone)

In another aspect, the sulfuric acid is diluted up to 80% with water. In yet another aspect, the sulfuric acid is diluted from 30 to 60% with water. In a further aspect, the sulfuric acid is diluted with 50% water.

The solvent can be selected from the group consisting of methanol, ethanol, acetone, n-propanol and isopropanol. In another aspect, the solvent is methanol.

In a further aspect, the reaction temperature is maintained between about −50 to about 60° C., −10 and 30° C., or from about 0 to about 15° C.

In yet another aspect, the inorganic base is selected from the group consisting of sodium hydrogen carbonate, sodium phosphate or ammonia. In a further aspect, the inorganic base is ammonia with a concentration between about 5 and 30%. In a further aspect, the inorganic base is 30% ammonia.

In another aspect, the reaction with the inorganic base is performed at a temperature up to about 30° C., and at a temperature from about 0 to about 15° C.

In yet another aspect, the compound of Formula II is extracted from the reaction solution with ethyl acetate.

In another aspect, the compound of Formula II (onapristone) is extracted from the reaction solution by allowing onapristone to crystallize.

In a further aspect, the reaction solution containing onapristone can be concentrated (e.g., increasing the amount of onapristone in the solution using vacuum distillation).

Previously described acetic acid methods of making onapristone provided poor yields of onapristone, for example, 51% yield after treatment of steroid 1 with 70% acetic acid at 60° C. (data not shown). In addition, the acetic acid method reaction is slow, requiring extension from one to two hours. Moreover, purifying onapristone from acetic acid method reaction did not improve the quality of the product. For example, new impurities were formed due to reactions with the C17-OH group.

The main products from the acetic acid method side reactions include C17 OAc and C17 ether, resulting from rearrangement. These by-products are difficult to remove, and prevent crystallization of the crude ONA resulting in the low yields of the reaction after purification.

Other methods (e.g., hydrochloric acid, oxalic acid or p-toluenesulfonic) produced either highly impure material or an incomplete reaction. Use of these acid catalysts are reported to be efficient for removal of the protecting group in the C3 position and the dehydration of the C5 OH group. However, these methods are not suitable for compounds having a THP-ether protecting group.

In one aspect, the reaction can be performed in aqueous solvent (methanol, ethanol, acetone, n-propanol or isopropanol) or in neat alcohol with concentrated or diluted sulfuric acid. In another aspect, the reaction is preferably run in methanol or ethanol. In yet another aspect, the most preferable solvent is neat methanol.

The amount of sulfuric acid has an influence of the reaction time. In one aspect, the reaction can be run with 0.1 equivalents to 10 equivalents of sulfuric acid either diluted with water or neat. In another aspect, the reaction is preferably run with diluted sulfuric with 10-90% sulfuric acid in water with 1-5 equivalents of sulfuric acid. In yet another aspect, the reaction performs best with 3 equivalents of sulfuric acid diluted 1:1 with water.

The temperature and the reaction time are important parameters for the reaction. The lower the temperature, the slower the reaction. In one aspect, the reaction can be run at about −50 to about 60° C. for about 10 minutes to about 10 hours. In another aspect, the reaction can be run at −10 to about 30° C. for about 30 minutes to about 5 hours. In another aspect, the reaction can be run at about 0-15° C. for about 1-2 hours.

The workup can be performed, for example, through the addition of aqueous inorganic bases (e.g., sodium bicarbonate, sodium phosphate, or ammonia). The temperature can be controlled to minimize the formation of impurities.

In another aspect, the inorganic base is added slowly to the acidic reaction mixture under temperature controlled conditions (e.g., 0-50° C., or 0-15° C.).

In another aspect, the temperature can be controlled from 0-50° C.

Acid hydrolysis to dehydrate position 5 and remove protecting groups to yield onapristone (ONA).

In another aspect, methods described herein provide about an 80% yield and about 88.9% purity. The described methods omit the need for chromatographic purification as the crude ONA product is directly crystallized.

EXAMPLES

The following non-limiting examples illustrate aspects described herein. Not every element described herein is required. Indeed, a person of skill in the art will find numerous additional uses of and variations to the methods described herein, which the inventors intend to be limited only by the claims. All references cited herein are incorporated by reference in their entirety.

Example 1—Deprotection and Dehydration 24 kg of a methanol solution containing 6.21 kg of AR-18-1109 (Steroid 1) and 4 L THF was concentrated in a vacuum. 20 L methanol and 20 mL pyridine was added to the residue, and the mixture was concentrated in a vacuum. 20 L methanol and 20 mL pyridine were added to the resulting residue, and this mixture was concentrated in a vacuum. 6 L methanol and 19 mL pyridine was added to to the resulting residue, and the solution was cooled to 5° C. under a nitrogen atmosphere.

50% sulfuric acid was added slowly to the resulting solution while maintaining the temperature between 5-10° C. The reaction was allowed to proceed for 1 hour. Next, a solution of 5.0 L water and 5.0 L ammonia (28-30%) was slowly added to the solution, while maintaining the temperature below 15° C., resulting in formation of a suspension.

Next, 20 L of water and 20 L of ethyl acetate were added. After stirring, the phases were allowed to settle and separate. The aqueous layer was extracted twice with 20 L ethyl acetate. The combined organic phases were washed with 3.5 L water and 10.5 L water. Washing was continued with 2.5 L brine and 7.5 L of water. The organic layer contained about 4.7 kg of crude ONA (purity 88.9%). This material was pooled with 4.8 kg of crude material (purity 89.9%) obtained with the same procedure performed with another batch of starting material.

The resulting solution of pooled product was concentrated until crystallization occurred. The crystallized solids were isolated, yielding 5.3 kg (purity 96.1%) of onapristone. After allowing the filtrate to stand overnight, the solids formed yielded another 0.78 kg of onapristone upon additional filtration. The mother liquor contained another 2.46 kg of onapristone which was collected as described below.

15.1 L THF and 15.2 L isopropyl acetate were added to the 6.07 kg of crude onapristone. The mixture was stirred at 54° C. until all material had dissolved. The THF was removed by vacuum distillation and addition of subsequent lots of isopropyl acetate. During distillation, onapristone started to crystallize yielding 5.12 kg of AR-18-1110 (Formula II) (purity 97.2%). The mother liquor contained about 0.97 kg of material (purity 84.9%) from which 0.78 kg of ONA was obtained.

What is claimed is:

1. A method of making onapristone comprising:
reacting the compound of Formula I:

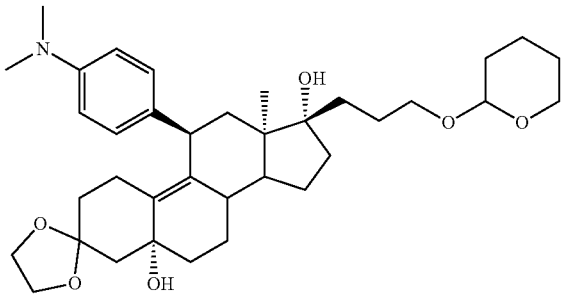 [SMILES: CN(C)c1ccc([C@H]2C[C@]3(C)C(CC[C@]3(O)CCCOC3CCCCO3)C3CC[C@@]4(O)CC5(CCC4=C32)OCCO5)cc1]

with sulfuric acid in a solution comprising pyridine and a solvent to deprotect and dehydrate the compound of Formula I;
maintaining the reaction temperature below about 60° C.;
neutralizing the reaction with an inorganic base to form a solution; and
extracting the compound of Formula II

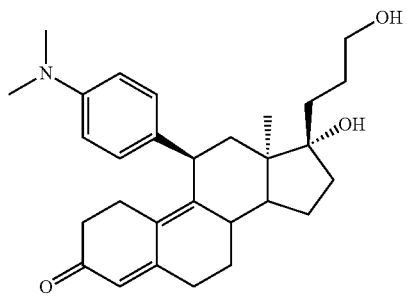 [SMILES: CN(C)c1ccc([C@H]2C[C@]3(C)C(CC[C@]3(O)CCCO)C3CCC4=CC(=O)CCC4=C32)cc1]

from the solution.

2. The method of claim 1, wherein the sulfuric acid is diluted up to 80% with water.

3. The method of claim 2, wherein the sulfuric acid is diluted from 30 to 60% with water.

4. The method of claim 3, wherein the sulfuric acid is diluted with 50% water.

5. The method of claim 1, wherein the solvent is selected form the group consisting of methanol, ethanol, acetone, n-propanol and isopropanol.

6. The method of claim 5, wherein the solvent is methanol.

7. The method of claim 1, wherein the temperature is maintained between about −50 to about 60° C.

8. The method of claim 7, wherein the temperature is maintained between about −10 and 30° C.

9. The method of claim 8, wherein the temperature is maintained from about 0 to about 15° C.

10. The method of claim 1, wherein the inorganic base is selected from the group consisting of sodium hydrogen carbonate, sodium phosphate or ammonia.

11. The method of claim 10, wherein the inorganic base is ammonia with a concentration between about 5 and 30%.

12. The method of claim 11, wherein the inorganic base is 30% ammonia.

13. The method of claim 1, wherein the reaction with the inorganic base is performed at a temperature from about 0 to about 30° C.

14. The method of claim 13, wherein the reaction with the inorganic base is performed at a temperature from about 0 to about 15° C.

15. The method of claim 1, wherein extraction of the compound of Formula II is performed with ethyl acetate.

16. The method of claim 1, wherein extraction of the compound of Formula II is performed by crystallization.

17. The method of claim 1, further comprising concentrating the solution.

18. The method of claim 17, wherein the solution is concentrated by vacuum distillation.

19. The method of claim 1, wherein the volume ratio of pyridine to the solvent is in a range of about 1:0.001 to about 1:0.03.

20. The method of claim 1, wherein the method further comprises reacting at least 1 kg of the compound of Formula I.

21. The method of claim 1, wherein the method provides a yield of about 80%.

22. The method of claim 1, wherein the method provides onapristone at a purity of about 88.9%.

* * * * *